US008736264B2

(12) United States Patent
Walsh et al.

(10) Patent No.: US 8,736,264 B2
(45) Date of Patent: May 27, 2014

(54) NMR LOGGING APPARATUS (75) Inventors: David O. Walsh, Mukilteo, WA (US); Peter Turner, Lynnwood, WA (US)

(73) Assignee: Vista Clara Inc., Mukilteo, WA (US)

( * ) Notice: Subject to any disclaimer, the term of this patent is extended or adjusted under 35 U.S.C. 154(b) by 43 days.

(21) Appl. No.: 13/356,381

(22) Filed: Jan. 23, 2012

(65) Prior Publication Data
US 2013/0187647 A1 Jul. 25, 2013

(51) Int. Cl.
*G01V 3/32* (2006.01)
*G01N 24/08* (2006.01)
*G01R 33/36* (2006.01)
*G01R 33/341* (2006.01)
*G01R 33/38* (2006.01)

(52) U.S. Cl.
CPC *G01N 24/08* (2013.01); *G01V 3/32* (2013.01); *G01R 33/3628* (2013.01); *G01R 33/341* (2013.01); *G01R 33/3808* (2013.01)
USPC .......................................................... 324/303

(58) Field of Classification Search
CPC ..... G01N 24/08; G01V 3/32; G01R 33/3628; G01R 33/341; G01R 33/3808
USPC ............... 324/303, 307, 309, 312; 166/57–60
See application file for complete search history.

(56) References Cited

U.S. PATENT DOCUMENTS

| 3,667,035 | A | * | 5/1972 | Slichter | 324/303 |
|---|---|---|---|---|---|
| 4,710,713 | A | | 12/1987 | Strikman | |
| 5,055,787 | A | | 10/1991 | Kleinberg et al. | |
| 5,055,788 | A | | 10/1991 | Kleinberg | |
| 6,018,243 | A | | 1/2000 | Taicher | |
| 6,023,164 | A | | 2/2000 | Prammer | |
| 6,081,116 | A | | 6/2000 | Wu et al. | |
| 6,160,398 | A | * | 12/2000 | Walsh | 324/309 |
| 6,291,994 | B1 | | 9/2001 | Kim | |
| 6,373,248 | B1 | * | 4/2002 | Poitzsch et al. | 324/303 |
| 7,463,027 | B2 | | 12/2008 | Prammer | |
| 7,466,128 | B2 | * | 12/2008 | Walsh | 324/309 |
| 7,986,143 | B2 | * | 7/2011 | Walsh | 324/318 |
| 8,096,349 | B2 | * | 1/2012 | Considine et al. | 166/60 |
| 2002/0101236 | A1 | * | 8/2002 | Wollin | 324/303 |
| 2008/0224696 | A1 | * | 9/2008 | Edwards | 324/303 |
| 2011/0109311 | A1 | * | 5/2011 | Walsh | 324/309 |
| 2012/0001629 | A1 | * | 1/2012 | Hopper et al. | 324/303 |
| 2012/0286779 | A1 | * | 11/2012 | Walsh et al. | 324/309 |

* cited by examiner

*Primary Examiner* — Melissa Koval
*Assistant Examiner* — Rishi Patel
(74) *Attorney, Agent, or Firm* — Jensen & Puntigam (57) ABSTRACT

Technologies including NMR logging apparatus and methods are disclosed. Example NMR logging apparatus may include surface instrumentation and one or more downhole probes configured to fit within an earth borehole. The surface instrumentation may comprise a power amplifier, which may be coupled to the downhole probes via one or more transmission lines, and a controller configured to cause the power amplifier to generate a NMR activating pulse or sequence of pulses. Impedance matching means may be configured to match an output impedance of the power amplifier through a transmission line to a load impedance of a downhole probe. Methods may include deploying the various elements of disclosed NMR logging apparatus and using the apparatus to perform NMR measurements.

46 Claims, 6 Drawing Sheets

NMR LOGGING APPARATUS

STATEMENT OF GOVERNMENT SUPPORT

This invention was made in part with Government support under Agreement DE-FG02-07ER84931 awarded by the US Department of Energy. The Government has certain rights in this invention.

BACKGROUND

Nuclear Magnetic Resonance (NMR) systems have been in use for many years and can be used to provide imaging and/or analysis of a sample being tested. For example, U.S. Pat. Nos. 6,160,398, 7,466,128, 7,986,143, U.S. patent application Ser. Nos. 12/914,138, and 13/104,721 describe a variety of NMR technologies, and are incorporated herein by reference. Various different types of NMR include medical NMR, often referred to as Magnetic Resonance Imaging (MRI), and NMR for measuring properties of earth formations, which provides, for example, geophysical techniques for detecting properties of the earth's crust. This disclosure relates to the latter type of NMR, and so the term "NMR" as used herein refers to NMR in the geophysical context. While there is some overlap in the technologies that may be applied in MRI and NMR, the samples being measured and the environments in which measurements are performed are different, leading to many differences in the technologies applied.

In general, NMR measurement involves generating a static magnetic field within a sample volume, emitting Radio-Frequency (RF) electromagnetic pulses into the sample volume, and detecting RF NMR responses from the sample volume. Most commonly, NMR measurement involves emitting multiple RF pulses in rapid succession and measuring the RF NMR responses between the RF pulses. The measured RF NMR responses provide useful information about the sample volume.

NMR measurements may be used to detect properties including, for example, the abundance of hydrogen contained within a sample volume as well as fluid composition, porosity, and permeability of the sample volume. NMR measurements may also be used to detect certain other atomic species, including carbon and potassium.

The term NMR as used herein includes Nuclear Quadrupole Resonance (NQR), unless stated otherwise. NQR is often useful for detecting nitrogen, chlorine and other compounds. NQR measurement techniques are similar to those used for NMR in general. While NMR measurements generally include generating a static magnetic field, a static magnetic field is not always required or used for NQR measurements.

NMR logging is an established type of surface NMR measurement wherein an NMR measurement apparatus is lowered into a borehole in the earth, and NMR measurements are performed to determine properties within and/or surrounding the borehole. However, existing NMR logging apparatus have a number of drawbacks, including high expense and difficulty of operation.

For example, some previous NMR logging apparatus may include most or all apparatus components, including for example a controller, a power supply, a power amplifier, transmit and receive antennae, and Analog to Digital (A/D) converter(s), within a downhole sensor package designed to fit within a borehole. Such a downhole sensor package may be 5 inches or larger in diameter and may weigh from several hundred pounds to over one thousand pounds.

In addition to size and weight limitations, previous NMR logging apparatus do not enable economical long-term or wide area in-situ monitoring of subsurface properties. Long-term or wide area in-situ monitoring is uneconomical when many expensive components are included within a downhole sensor package, because either many expensive NMR logging apparatus must be purchased, or expensive components must be either left in place long-term, and therefore unavailable for other uses, or NMR logging apparatus must be repeatedly mobilized which involves mobilization and human labor costs.

SUMMARY

Technologies applicable to NMR logging are disclosed. Some example NMR logging apparatus may comprise surface instrumentation coupled to a downhole probe via a transmission line. The surface instrumentation may comprise a controller, a signal generator, a power supply, a power amplifier configured to generate one or more current and/or voltage waveforms, and receive electronics such as A/D converter(s) and memory for storing digitized NMR response data. The transmission line may be coupled with the power amplifier and may have a length at least one tenth of one wavelength of a current and/or voltage waveform generated by the power amplifier. The downhole probe may be configured to fit within an earth borehole, and may comprise one or more static magnetic field generation devices, such as one or more magnets, and one or more antennae coupled with the transmission line.

Example NMR logging apparatus may also include an impedance matching means configured to match an output impedance of the power amplifier through the transmission line to a load impedance of one or more of the antennae in the downhole probe. Impedance matching means may comprise a first matching means configured to match the output impedance of the power amplifier to a characteristic impedance of the transmission line, and/or a second matching means configured to match load impedance of one or more antennae in the downhole probe to the characteristic impedance of the transmission line. The first and/or second matching means may comprise an impedance matching circuit comprising transformers, combinations of inductors and capacitors, or combinations of transformers, inductors and capacitors. Impedance matching means may comprise a transmission line length that is approximately a positive integer number of quarter wavelengths of a current and/or voltage waveform generated by the power amplifier. Impedance matching means may comprise one or more antennae in the downhole probe that are configured to present a load impedance approximately equal to a characteristic impedance of the transmission line during a transmit mode.

An example downhole probe may comprise means for detecting NMR signals induced in the antennae. A preamplifier may be configured to amplify detected NMR signals. In some embodiments, an output impedance of the preamplifier may be matched to a characteristic impedance of a second transmission line configured to transmit detected NMR signals from the downhole probe to the surface instrumentation. A downhole probe may also comprise one or more Analog to Digital (A/D) converter(s). Electronics within a downhole probe may be coupled with a power supply on the surface, or may comprise a local power supply such as one or more batteries.

In some embodiments, a plurality of downhole probes may be coupled with the power amplifier via a plurality of transmission lines, and the surface instrumentation may be configured to perform NMR measurements with the plurality of downhole probes. A switching device may be coupled between the plurality of transmission lines and the power amplifier, and the switching device may be configured to selectively connect the power amplifier to one or more of the transmission lines.

Some example NMR measurement methods may include deploying surface instrumentation on or above the surface of the earth, the surface instrumentation comprising a controller and power amplifier configured to generate one or more NMR-activating current and/or voltage waveforms; deploying a downhole probe inside an earth borehole, the downhole probe comprising one or more antennae, and detection means configured to detect NMR signals induced on the antennae; deploying a transmission line configured to transfer a current and/or voltage waveform between the power amplifier and the downhole probe, the transmission line having a physical length equal to or greater than one tenth of the wavelength of the transferred current and/or voltage waveform within the transmission line; deploying an impedance matching means at one or both ends of the transmission line, the impedance matching means configured to match an output impedance of the power amplifier through the transmission line to a load impedance of one or more of the antennae in the downhole probe during a transmit mode; and using the surface instrumentation and downhole probe coupled via the transmission line and impedance matching means to perform NMR measurements of one or more properties within and/or surrounding the earth borehole. The one or more properties may include NQR properties, which are one type of NMR property as described herein.

Some example NMR measurement methods may include deploying surface instrumentation on or above the surface of the earth, the surface instrumentation comprising a controller and power amplifier configured to generate one or more NMR activating current and/or voltage waveforms; deploying a plurality of downhole probes inside one or more earth boreholes, each of the downhole probes comprising one or more antennae, and detection means configured to detect NMR signals; deploying a plurality of transmission lines configured to transfer current and/or voltage waveforms between the power amplifier and the downhole probes; and using the surface instrumentation and downhole probes coupled via the transmission lines to perform NMR measurements of one or more properties within and/or surrounding the earth borehole(s). In some embodiments, at least one of the transmission lines may have a physical length equal to or greater than one tenth of the wavelength of a current and/or voltage waveform, and an impedance matching means may be deployed to match an output impedance of the power amplifier through the at least one transmission line to a load impedance of one or more of the antennae in a downhole probe during a transmit mode of the surface instrumentation.

Some example NMR measurement methods may include using at least one of the downhole probes to perform a plurality of NMR measurements at a same location in an earth borehole, wherein the measurements are separated in time. The plurality of NMR measurements may be used to detect a change over time of measured properties. Measured properties may include, e.g., NMR properties, NQR properties, physical properties, hydraulic properties, or chemical properties.

Further aspects and variations are discussed in detail below.

BRIEF DESCRIPTION OF THE DRAWINGS

Various features and attendant advantages of the disclosed technologies will become fully appreciated when considered in conjunction with the accompanying drawings, in which like reference characters designate the same or similar parts throughout the several views, and wherein.

DETAILED DESCRIPTION

Prior to explaining embodiments of the invention in detail, it is to be understood that the invention is not limited to the details of construction or arrangements of the components and method steps set forth in the following description or illustrated in the drawings. The invention is capable of other embodiments and of being practiced and carried out in various ways. Also, it is to be understood that the phraseology and terminology employed herein are for the purpose of the description and should not be regarded as limiting.

Technologies including NMR logging apparatus and methods are disclosed. Example NMR logging apparatus may include surface instrumentation and one or more downhole probes configured to fit within an earth borehole. The surface instrumentation may comprise a power amplifier, which may be coupled to the downhole probes via one or more transmission lines, and a controller configured to cause the power amplifier to generate a NMR activating pulse or sequence of pulses. Impedance matching means may be configured to match an output impedance of the power amplifier through a transmission line to a load impedance of a downhole probe. Methods may include deploying the various elements of disclosed NMR logging apparatus and using deployed NMR logging apparatus to perform NMR measurements.

Figure 1:
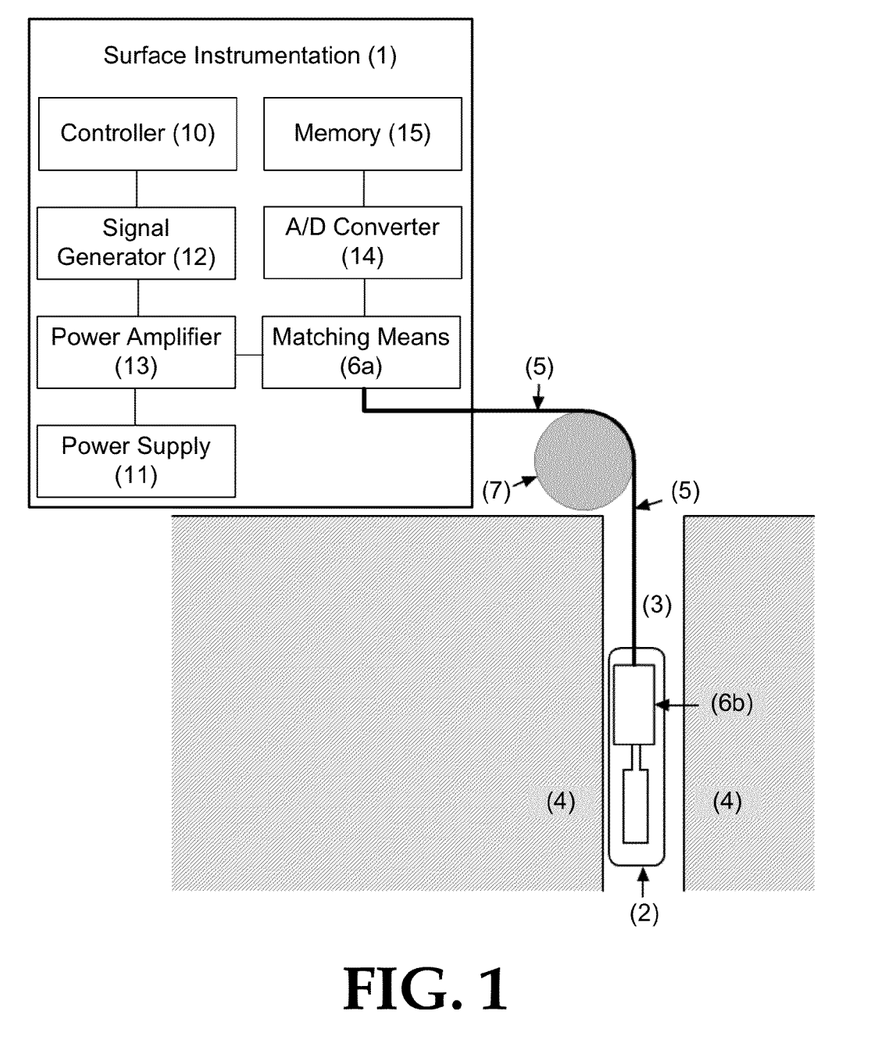
FIG. 1 illustrates an example NMR logging apparatus and locations of components thereof relative to the surface of the earth.

FIG. 1 illustrates an example NMR logging apparatus and locations of components thereof relative to the surface of the earth, in accordance with various embodiments of this disclosure. The NMR logging apparatus in FIG. 1 includes: surface instrumentation (1), located near the surface of the earth; a downhole probe (2) which is lowered into an earth borehole (3) to measure properties of within and/or surrounding the borehole, e.g., properties of earth formation (4), and an electrically long transmission line (5) with impedance matching means (6a, 6b) at one or both ends of the transmission line (5).

An optional draw works (7) may be employed to deploy and retrieve the transmission line (5) and downhole probe (2). In some embodiments, the illustrated NMR logging apparatus may be configured to perform NMR measurements, for example to characterize subsurface fluids and geologic formations.

The surface instrumentation (1) includes a controller (10) such as a computer or digital processor which is programmed to produce NMR pulse sequences appropriate and useful for performing NMR measurements in earth formations. The controller may also control other aspects of NMR measurement, such as by controlling switches such as the switch (22) illustrated in FIG. 2 and the switching device (7) illustrated in FIG. 10.

In some embodiments, NMR pulse sequences may comprise a CPMG sequence in which a series of pulses are generated, separated by a duration ("echo-time") that may be on the order of a two milliseconds or shorter. The echo-time spacing may be short to optimize the signal to noise ratio and to reduce artifacts associated with molecular diffusion in fluids. Using a short-echo time, however, increases the effective duty cycle placed on the power generation components (11, 13) and so the power generation components (11, 13) may be configured to support short-echo times in some embodiments. For example, long term power capacity of an NMR logging apparatus may be increased by adding energy storage capacitors to the surface instrumentation (1).

The surface instrumentation (1) may include an appropriate power supply (11) to power the various components of the surface instrumentation (1), and optionally also the downhole probe (2).

The surface instrumentation (1) also includes digital and/or analog output signal generator (12), which may be controlled by the controller (10), and which may produce low voltage NMR pulse sequence activating signals as input to the power amplifier (13). In some embodiments, a signal generator (12) may be implemented by the controller (10) or a separate signal generator device.

The surface instrumentation (1) may also include a power amplifier (13) configured to produce amplified NMR excitation waveforms as current and/or voltage waveforms. The power amplifier (13) may be configured to use signals produced by signal generator (12) and power from the power supply (11) to produce amplified signals. Areas directly surrounding a downhole probe (2) may contain fluids in the borehole annulus (3) or regions of the earth formation (4) surrounding the borehole (3) that were disturbed during drilling. Therefore it may be preferable in some circumstances to investigate a zone several inches or more away from the center of the downhole probe (2). RF fields generated by passing amplified RF current through downhole probe antennae decrease in amplitude further from the downhole probe (2) due to geometric attenuation. Therefore power supplies for a downhole probe (2) may, in some circumstances, be capable of generating sufficiently high current pulses for the RF fields to penetrate the earth formation (4). Hence, it is preferable in some NMR logging apparatus to employ a power amplifier (13) capable of producing peak power of 2 kW or higher.

The surface instrumentation (1) may include receive electronics such as A/D converter (14) configured to convert NMR response signals received from the downhole probe (2) from analog to digital form, and a memory 15 configured to store digitized NMR response data. Digitized NMR response data may be stored in a memory (15), such as a memory in a computer, and may be processed and analyzed in a variety of useful ways. The memory (15) may in some embodiments be included in a computer along with controller (10), and such a computer may also comprise software for analysis of received NMR response data.

Depending on the specific embodiment, A/D converters (14) may be located at the surface or with downhole probe electronics. In embodiment wherein A/D converters (14) are located at the surface, a second electrically long transmission line (such as 5b in FIG. 2) may be used to transmit an analog receive signal from the downhole probe to the surface, and impedance matching means may be used to maximize the efficiency of transmission of the receive signal from the downhole probe (2) to the surface. In embodiments wherein the A/D converters (14) are located within the downhole probe (2), the A/D converters (14) may be configured to operate automatically, or the surface instrumentation (1) may comprise a controller (such as controller (10) or a separate controller) configured to remotely control the one or more A/D converters (14) in the downhole probe (2). A controller may be configured to synchronize operation of A/D converters (14) with a transmit cycle though an auxiliary clock line extending to downhole probe (2), or though bootstrap clock signals and/or triggers combined with a transmitted NMR pulse sequence.

The transmission line (5) may be an electrical transmission line with characteristic impedance Zo. The term "electrically long" as used herein refers to a physical length greater than one tenth of a wavelength of a current and/or voltage waveform produced by the power amplifier (13) at a transmitting operating frequency. This is the approximate the length at which wave reflections and phase delays become significant.

The impedance matching means (6a, 6b) employed at one or both ends of the transmission line (5) may be configured to approximately match the load impedance Zl of transmitting antennae in the downhole probe (2), as seen through the transmission line (5), to the output impedance Zs of the surface-based power amplifier (13).

The downhole probe (2) may be designed to fit in a cased or uncased earth borehole, and may contain a magnet assembly configured to generate an elevated static background magnetic field in a sample volume within earth formation (4), one or more antennae configured to use the amplified excitation waveforms to emit RF signals into the sample volume within earth formation (4), and one or more antennae configured to detect an NMR response from the sample volume within earth formation (4).

In some embodiments, tuning capacitors may be included at the surface and/or within the downhole probe (2) to maximize power transfer between the surface based power amplifier (13) and the downhole probe antennae.

In some embodiments, NMR logging apparatus according to this disclosure may be configured for use with small and very small diameter boreholes. A small diameter borehole is defined herein as less than 5 inches in diameter, and a very small diameter borehole is defined herein as 2 inches or less in diameter. Therefore some downhole probes according to this disclosure may be either less than 5 inches in diameter or 2 inches or less in diameter, depending on the specific embodiment. Additionally, downhole probes according to this disclosure may be configured with low weight, e.g., less than 100 pounds, and relatively low production cost.

Figure 2:
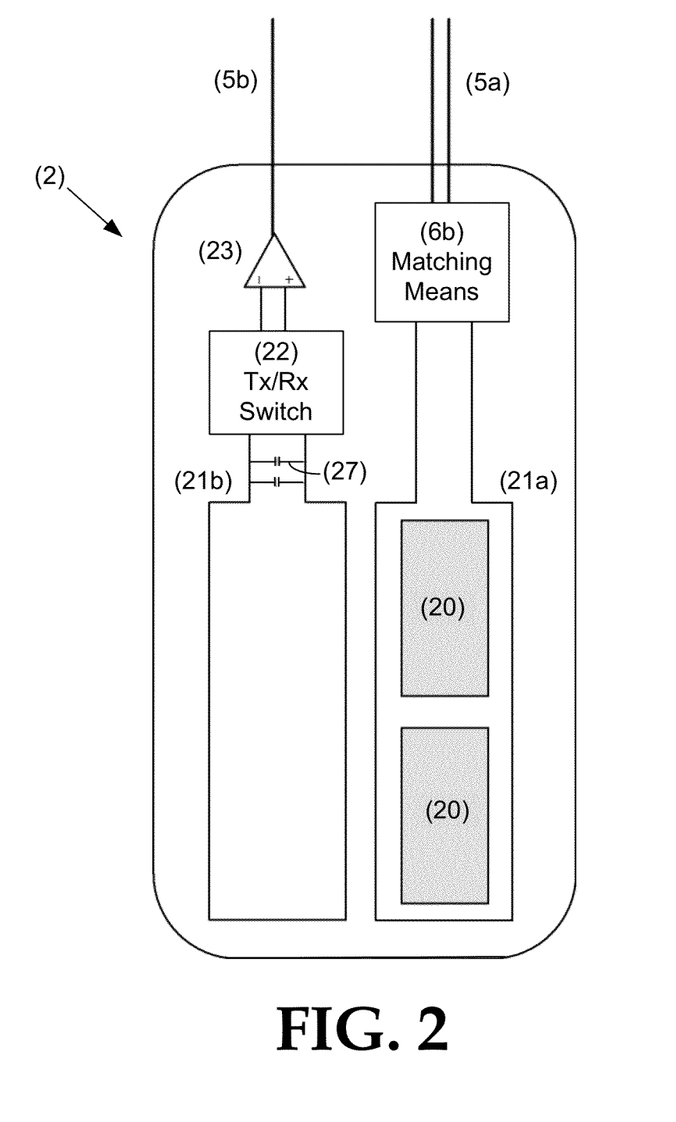
FIG. 2 illustrates an example downhole probe including separate transmitting and receiving antennae.

FIG. 2 illustrates an example downhole probe (2) including separate transmitting and receiving antennae, in accordance with various embodiments of this disclosure. FIG. 2 includes a downhole probe (2) comprising a matching means (6b), a transmitting antenna (21a), an array of one or more static magnetic field generating devices (20), a receiving antenna (21b) including tuning capacitors (27), a transmit/receive switch (22), and a preamplifier (23). A transmission line (5a) is coupled with transmitting antenna (21a) via matching means (6b). A second transmission line (5b) is coupled with receiving antenna (21b) via transmit/receive switch (22) and preamplifier (23).

In some embodiments, multiple transmission lines (5a, 5b) may be used. A first transmission line (5a) may couple a transmitting antenna (21a) in the downhole probe (2) with a surface based power amplifier (13). A second transmission line (5b) may couple a receiving antenna (21b) in the downhole probe (2) with surface based receive electronics, such as a surface based A/D converter (14). Either or both of the transmission lines (5a, 5b) may be electrically long transmission lines, and either or both of the transmission lines (5a, 5b) may be coupled with impedance matching means, as described herein. In some embodiments, differently configured impedance matching means may be employed for different transmission lines (5a, 5b). Either or both of the transmission lines (5a, 5b) may comprise a cable in some embodiments.

Depending upon the impedance matching means selected for a particular embodiment of the invention, matching means (6b) may be incorporated within the downhole probe (2) to perform some or all of the impedance matching between the transmission line (5a), the transmitting antenna (21a), and the surface based power amplifier (13).

The downhole probe (2) may include an array of one or more static magnetic field generating devices (20). Magnetic field generating devices (20) may include permanent magnets and/or electromagnets.

The downhole probe (2) may include a transmitting antenna (21a) which is configured to generate RF magnetic fields during a transmit mode to cause precession of NMR active nuclei, and a receiving antenna (21b) which is configured to detect the resulting magnetic fields generated by the NMR processes during a receive mode. Transmitting and receiving functions may be accomplished by a same antenna, or by separate transmitting and receiving antennae as shown in FIG. 2.

The antennae (21a) and (21b) may be single turn, or multiple turn induction loops, also referred to herein as current loops and/or coils, and may also be partial coaxial type antennae, or any other type of antenna or induction coil suitable for generating RF magnetic fields in an earth formation and for detecting NMR responses from an earth formation. The antennae (21a) and (21b) may optionally include tuning capacitors (27) or other appropriate tuning mechanisms. In some embodiments, the transmitting antenna (21a) and receiving antenna (21b) may be inductively coupled with a non-zero mutual inductance during a transmit mode, as described further herein.

The downhole probe (2) may include a transmit/receive switch (22) to isolate receive electronics such as the preamplifier (23) and other receive electronics that may be coupled therewith, from high voltage on the receiving antenna (21b) during transmit mode, and to couple the receiving antenna (21b) to the receive electronics during receive mode.

The downhole probe (2) may include a preamplifier (23) to amplify to detected NMR signals to suitable levels for digitization and/or for analog transmission to surface instrumentation (1). The transmit/receive switch (22) and preamplifier (23) are example means for detecting NMR signals induced in at least one of the antennae in the downhole probe (2). In some embodiments, an output impedance of the preamplifier (23) may be matched to a characteristic impedance of the second transmission line (5b).

The downhole probe (2) may comprise means for coupling energy from the transmission lines (5a, 5b) into at least one of the antennae (21a, 21b). For example, an electrical interface (not shown) may be configured to connect and disconnect the transmission lines (5a, 5b) from the downhole probe (2), so the components can be separated for transport and storage.

In some embodiments, the downhole probe (2) may include a means (not shown) for reducing the Q-factor of the transmitting and/or receiving antennae (21a, 21b). This Q-damping means may comprise passive electronics and/or actively controlled electronics circuits. The Q-damping electronics circuits may be electrically connected to one or more of the receiving antenna, for example as described in U.S. Pat. No. 5,055,788, or inductively coupled to one or more of the transmitting and/or receiving antennae as described in U.S. Pat. No. 6,291,994. The Q-damping means may be active during either all or part of the transmit mode, during all or part of the receive mode, or during part or all of both modes. Passive Q-damping circuits may include diode-based circuits that increase effective circuit resistance when a transmitting voltage exceeds a diode turn-on voltage. Actively controlled Q-damping circuits may be controlled via external timing from a surface-based controller, such as controller (10), or automatically triggered from the timing of a transmitted pulse sequence.

Figure 3:
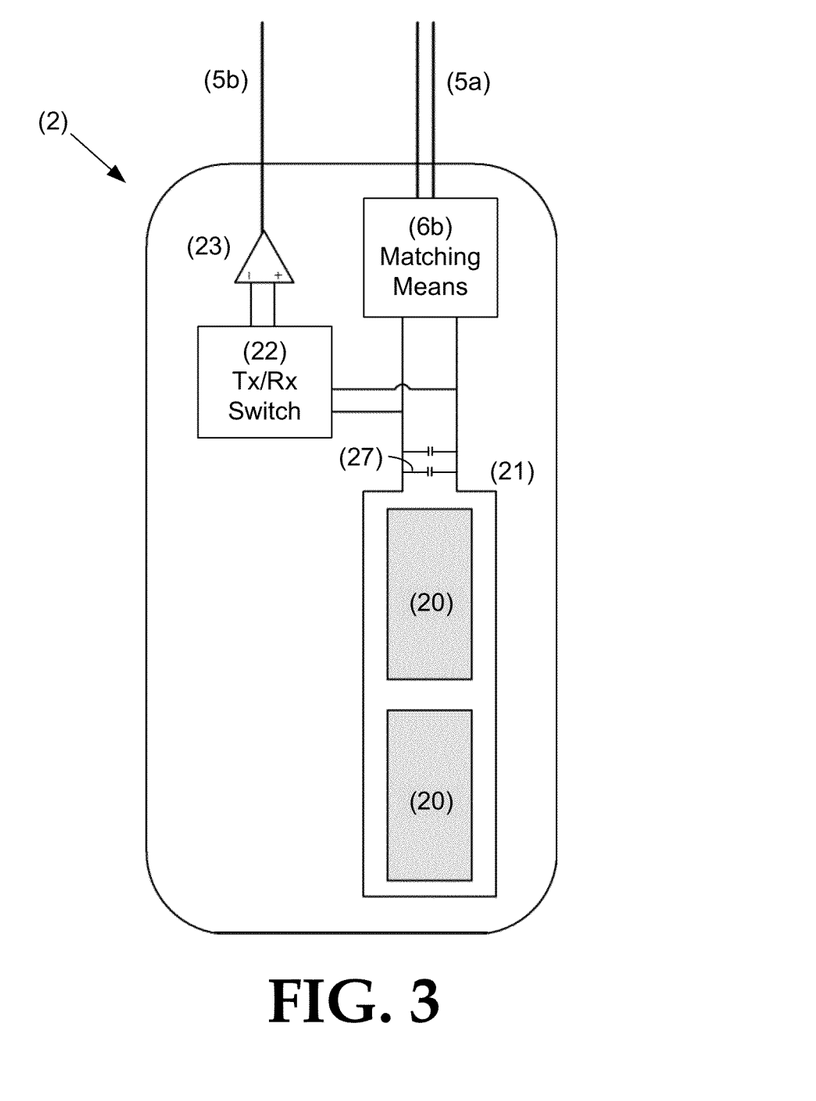
FIG. 3 illustrates an example downhole probe including a combination transmitting/receiving antenna.

FIG. 3 illustrates an example downhole probe including a combination transmitting/receiving antenna, in accordance with various embodiments of this disclosure. FIG. 3 includes a downhole probe (2) comprising a matching means (6b), transmitting/receiving antenna (21) configured to perform both transmitting and receiving functions and including tuning capacitors (27), an array of one or more static magnetic field generating devices (20), a transmit/receive switch (22), and a preamplifier (23). A transmission line (5a) is coupled with transmitting/receiving antenna (21) via matching means (6b). A second transmission line (5b) is coupled with transmitting/receiving antenna (21) via transmit/receive switch (22) and preamplifier (23).

Figure 4:
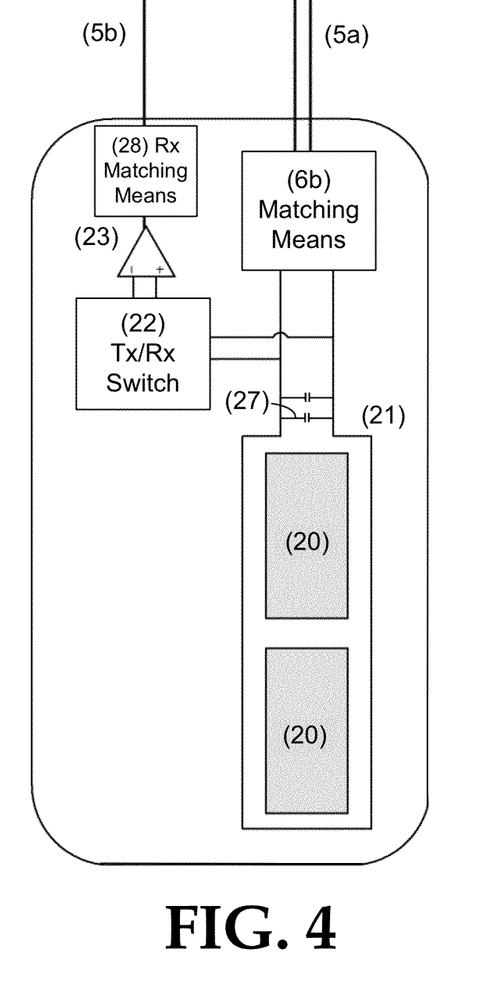
FIG. 4 illustrates an example downhole probe including a receive circuit matching means configured to match load impedance of one or more antennae in a downhole probe to a characteristic impedance of a transmission line.

In FIG. 3, matching means (6b) may be configured to perform some or all of the impedance matching between the transmitting/receiving antenna (21), the transmission line (5a), and the surface based power amplifier (13). In FIG. 2 and FIG. 3, the static magnetic field generating devices (20) and the transmitting and receiving antennae (21, 21a, 21b) may be arranged and designed in any form that is useful and convenient for measuring NMR properties of an earth formation. This disclosure is not dependent on any specific arrangement of magnets and antennae. Embodiments may utilize any magnet and antenna designs known in the art or as may be developed in the future. For example, designs disclosed in U.S. Pat. Nos. 4,710,713 and 5,055,788, may be applied in the context of some embodiments of the present disclosure, FIG. 4 illustrates an example downhole probe including a receive circuit matching means configured to match load impedance of one or more antennae in a downhole probe to a characteristic impedance of a transmission line, in accordance with various embodiments of this disclosure. FIG. 4 includes a downhole probe (2) comprising a matching means (6b), a transmitting/receiving antenna (21) including tuning capacitors (27), an array of one or more static magnetic field generating devices (20), a transmit/receive switch (22), a preamplifier (23), and a receive circuit matching means (28). A transmission line (5a) is coupled with transmitting/receiving antenna (21) via matching means (6b). A second transmission line (5b) is coupled with transmitting/receiving antenna (21) via transmit/receive switch (22), preamplifier (23) and receive circuit matching means (28).

The receive circuit matching means (28) may be configured to match an output impedance of downhole probe receive electronics, such as the preamplifier (23) and/or buffer amplifier (not shown) in the receive side of the downhole probe (2) to an impedance of the second transmission line (5b) and/or or to an impedance of surface receive electronics (not shown) within the surface instrumentation (1) as reflected through the second transmission line (5b). The second transmission line (5b) may comprise an electrically long analog receive cable. A/D conversion and storage of the detected NMR signals may be performed by receive electronics located at the surface, e.g., among surface instrumentation (1).

Embodiments according to FIG. 4 are useful for consolidating additional receive electronics, specifically A/D converter devices (14), at the surface, e.g., among surface instrumentation (1). Stationing the A/D converters (14) at the surface simplifies their control and synchronization by a surface-based controller (10), and potentially allows the downhole probe (2) to be smaller and simpler.

Referring to FIG. 1-FIG. 4, the downhole probe (2) contains a magnet assembly which causes alignment and polarization of NMR susceptible species in the adjacent earth formation (4). The downhole probe (2) also contains a transmitting antenna (21a) and a receiving antenna (21b). In some embodiments these can be the same antenna (21).

The controller (10) at the surface is programmed to control digital and/or analog signal generator devices (12), which produce appropriate low-voltage signals for generation of NMR pulse sequences. The RF power amplifier (13) at the surface is configured to convert the low voltage NMR pulse sequence signals from the signal generating devices (12) into higher powered NMR pulse sequences. The output of the power amplifier (13) is generally load-dependent electrical current and voltage waveforms, also referred to herein as RF current waveforms.

The transmitting antenna (21a) within the downhole probe (2) is electrically connected to the electrically-long transmission line (5a), and is driven directly from the surface by the power amplifier (13), through the transmission line (5a). The RF current waveforms are generated by the power amplifier (13) at the surface and transferred by the transmission line (5a) to the transmitting antenna (21a) in the downhole probe (2), which converts the electrical energy from the power amplifier (13) into local Alternating Current (AC) magnetic fields which activate NMR processes in the earth formation (4).

One or more matching means (6a, 6b) are employed so as to approximately match the output impedance of the power amplifier (13), through the transmission line (5a), to the input impedance of the transmitting antenna (21a).

The receiving antenna (21b) within the downhole probe (2) is electrically connected to receive electronics within the downhole probe (2), such as preamplifier (23). One or more A/D converters (14), located either in within the downhole probe (2) or at the surface, are used to sample and store detected NMR signals.

FIG. 5-FIG. 8 illustrate example impedance matching means comprising one or more impedance matching circuits, in accordance with various embodiments of this disclosure. The illustrated impedance matching circuits may be used for example as impedance matching means (6a, 6b) illustrated in FIG. 1-FIG. 4.

Figure 5:
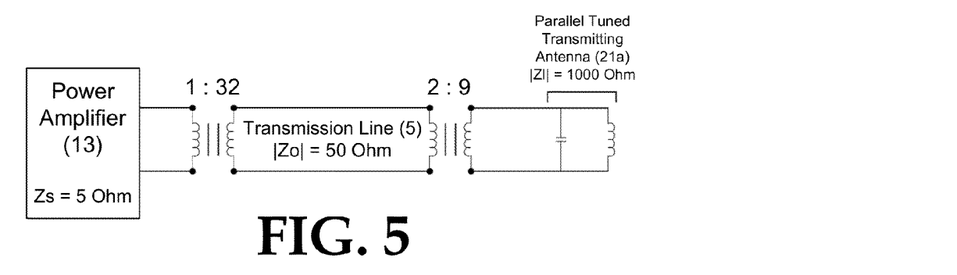
FIG. 5 illustrates an example impedance matching means comprising one or more impedance matching circuits.
Figure 6:
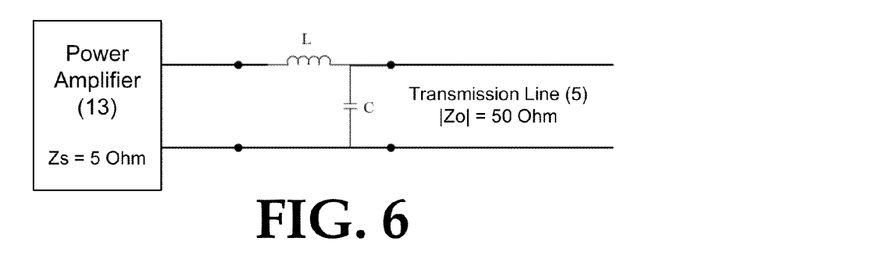
FIG. 6 illustrates an example impedance matching means comprising one or more impedance matching circuits.
Figure 7:
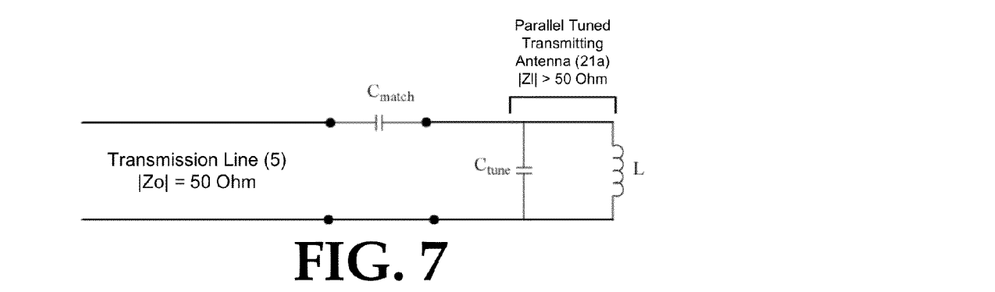
FIG. 7 illustrates an example impedance matching means comprising one or more impedance matching circuits.
Figure 8:
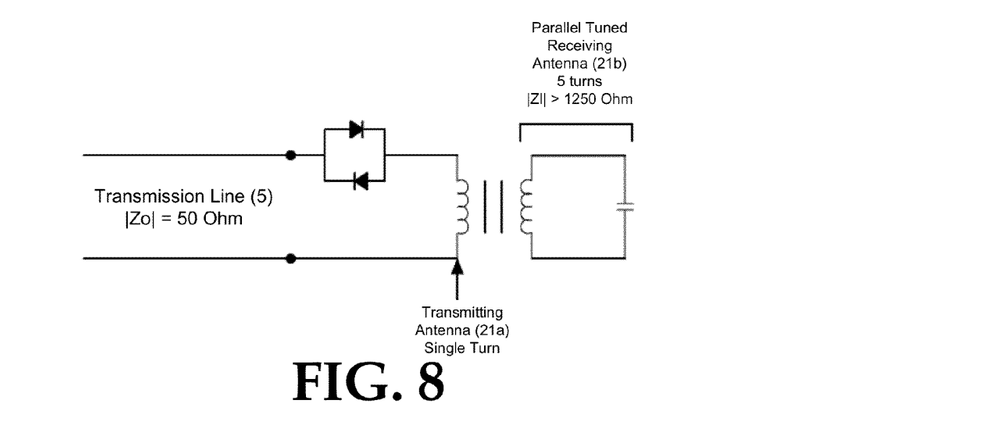
FIG. 8 illustrates an example impedance matching means comprising one or more impedance matching circuits.

In general, FIG. 5 illustrates impedance matching circuits comprising appropriate transformers configured to match impedances of both a power amplifier (13) and a transmitting antenna (21a) to a characteristic impedance of a transmission line (5). FIG. 6 illustrates impedance matching circuits comprising a series inductor and parallel capacitor configured to match a relatively low output impedance of a power amplifier (13) to a higher impedance transmission line (5). FIG. 7 illustrates an impedance matching circuits comprising a series matching capacitor configured to match a relatively high input impedance of a parallel tuned transmitting antenna to a lower impedance transmission line (5). FIG. 8 illustrates impedance matching circuits comprising a transformer-coupled pair of transmit and receive antennae configured to match a relatively high input impedance of a parallel tuned receive antenna (coil) to a lower impedance transmission line (5) during transmit mode. During receive mode, optional series crossed diodes are configured to isolate the receive antenna (21b) from the transmit antenna (21a) and transmission line (5).

Impedance matching means may comprise the impedance matching circuits illustrated in FIG. 5-FIG. 8, and variants thereof, comprising transformers, combinations of inductors and capacitors, or combinations of transformers, inductors and capacitors. However, impedance matching means are not limited to the illustrated impedance matching circuits. Impedance matching means may comprise any means to optimize the efficiency of transmitting waveforms, including transmit waveforms and received NMR response waveforms, through an electrically long transmission line (5).

For example, impedance matching means may comprise any means to optimize the efficiency of transmitting amplified RF NMR excitation waveforms, from a power amplifier (13) located at the surface, to a downhole probe (2), through an electrically long transmission line (5). There are many possible ways to cause the output impedance of the power amplifier (13) to be approximately matched to the impedance of a downhole probe antenna, such as a transmitting antenna (21a), a receiving antenna (21b), and/or a transmitting receiving antenna (21), as seen through the electrically long transmission line (5).

In some embodiments, impedance matching means may comprise an NMR logging apparatus design that is configured to match the output impedance of the power amplifier (13) to an input impedance of a transmitting antenna (21a). For example, NMR logging apparatus impedances may be matched to a common value Zo, where for example Zo may be equal to 50 ohms, or 75 ohms. In some embodiments of this design, the power amplifier (13) may be designed or selected to exhibit output impedance Zs equal to Zo, the long transmission line (5) would be designed or selected to exhibit a characteristic impedance of Zo, and the downhole probe antenna assembly may be designed or selected to exhibit an input impedance Zl equal to Zo. In some embodiments, an impedance matching means may therefore comprise one or more antennae in the downhole probe (2) that are configured to present a load impedance approximately equal to a characteristic impedance of the transmission line (5) during transmit mode.

In some embodiments, impedance matching means may comprise a first matching means configured to match the output impedance of the power amplifier (13) to a characteristic impedance of the transmission line (5), and a second matching means configured to match load impedance of one or more antennae in the downhole probe (2) to the characteristic impedance of the transmission line (5). For example, FIG. 5 illustrates the use of a first matching means comprising a transformer configured to match the output impedance of a power amplifier (13) (with comparatively low output impedance) to the impedance of a transmission line (5) with comparatively high impedance. For example, a transformer with a turns ratio of 1 to 3.2 will transform an output impedance of 5 ohms to approximately 50 ohms, to approximately match the impedance of a 50 ohm transmission line (5). Similarly, FIG. 5 also depicts a second matching means comprising a second transformer configured to match the input impedance of a transmitting antenna (21*a*) to the characteristic impedance of the transmission line (5). For example, as shown in FIG. 5, a transformer with a turns ratio of 2 to 9 will approximately match a transmitting antenna (21*a*) input impedance of 1000 ohms to a 50 ohm transmission line impedance.

In some embodiments, impedance matching means may be configured to use collections of reactive circuit elements to match the output impedance of the power amplifier (13) to the transmission line impedance, and/or to match the input impedance of a transmitting antenna (21*a*) to the transmission line impedance. For example, FIG. 6 illustrates an impedance matching circuit comprising a series inductor on the input, and a parallel capacitor on the output. The illustrated impedance matching circuit acts to match a low impedance input to a higher impedance output at a particular frequency. In FIG. 6, the impedance matching circuit is illustrated in the application of matching comparatively low power amplifier output impedance of 5 ohms to a comparatively higher characteristic transmission line impedance of 50 ohms. This type of impedance matching circuit may also be used to match transmitting antenna (21*a*) impedance to transmission line impedance.

In some embodiments, impedance matching means may be configured to use reactive circuit elements as matching means, the reactive circuit elements comprising a series capacitor. For example, FIG. 7 illustrates an impedance matching circuit comprising a series capacitor configured to match a comparatively high impedance of a parallel tuned transmitting antenna (21*a*) to a comparatively low impedance of a transmission cable.

In some embodiments, impedance matching means may comprise a transformer-coupled antenna assembly configured to match the impedance of a transmitting antenna (21*a*) to the impedance of the transmission line (5). For example, a transformer-coupled antenna assembly may comprise two mutually coupled coils, a transmitting antenna (21*a*) primary coil (which is electrically connected to the transmission line (5), and a receiving antenna (21*b*) secondary coil which is not electrically connected to the transmission line (5), but which functions as the detection coil in receive mode. The primary and secondary coils may be configured with differing numbers of turns and/or incomplete coupling. In transmit mode, the secondary coil presents a load to the transmission line (5), through mutual coupling with the primary coil. The turns ratio and/or coupling reduction factor cause the impedance of the secondary coil (21*b*) to be transformed to a different value when seen as a load on the primary coil input. This impedance transforming behavior can be used to match the relatively high input impedance of a parallel tuned secondary coil (21*b*) to the relatively low characteristic impedance of the transmission line (5).

For example, FIG. 8 illustrates the use of a transformer-coupled antenna assembly to match the comparatively high impedance of the secondary coil (the detection coil) to the comparatively low impedance of the transmission line (5). In the example of FIG. 8, the characteristic impedance of the transmission line (5) is 50 ohms, the impedance of the parallel tuned receiving antenna (21*b*) secondary coil is 1250 ohms, and a primary to secondary coil turns ratio of 1 to 5 serves to transform the secondary coil impedance of 1250 ohms to approximately 50 ohms, thus matching the secondary coil to the characteristic impedance of the transmission line (5) in transmit mode. The optional series crossed diodes depicted in FIG. 8 serve to isolate the secondary coil from the transmitting antenna (21*a*) primary coil and the transmission line (5), during receive mode only.

In some embodiments according to FIG. 8, separate transmit and receive antennas may be employed, wherein the transmitting antenna (21*a*) and receiving antenna (21*b*) may be inductively coupled with a non-zero mutual inductance during a transmit mode, and wherein the transmitting antenna (21*a*) is inductively coupled to the receive antenna (21*b*) during receive mode, and wherein the transmitting antenna (21*a*) does not significantly load the receive antenna (21*b*) during receive mode. For example, the one or more antennae (21*a*, 21*b*) in the downhole probe (2) may comprise a pair of inductively coupled loops, such that: a first loop (21*a*) is electrically connected to the transmission line (5), a second loop (21*b*) is electrically connected to a parallel tuning capacitor, a transmit/receive switch, and receive electronics, and a ratio of turns between the first and second loops is selected so as to approximately or partially match a relatively high impedance of the second loop (21*b*) to a relatively low impedance of the transmission line (5).

In some embodiments, impedance matching means for matching the impedance of a transmitting antenna (21*a*) to the power amplifier (13) may comprise an appropriately selected transmission line (5) length. For example, the length of the transmission line (5) may be approximately equal to one quarter of a wavelength, or any odd integer multiple of quarter wavelengths, at an operating frequency of the NMR logging apparatus. The transmitting antenna (21*a*) and/or power amplifier (13) may be configured such that the transmitting antenna (21*a*) impedance is transformed by the quarter wave transmission line to match the power amplifier output impedance. A transmission line (5) that is approximately one quarter of a wavelength in length at a particular operating frequency will transform the impedance Z2 attached to one end of the transmission line (5) to another impedance value Z1 at the input to the transmission line (5) according to the relation:

$$|Zo|^2 = Z1 * Z2$$

where Zo is the characteristic impedance of the transmission line (5), Z2 is the load impedance attached to one end of the transmission line (5), and Z1 is the input impedance seen at the other end of the transmission line (5). This impedance transforming property also occurs for transmission line lengths equal to any odd integer multiple of quarter wavelengths at an operating frequency of the NMR logging apparatus.

In some embodiments using a quarter wavelength transmission line to match the power amplifier output impedance to the transmitting antenna (21*a*) impedance, a power amplifier (13) and transmission line (5) may be configured such that the power amplifier output impedance Z1 is equal to the square of the transmission line impedance Zo divided by the probe impedance Z2:

$$Z1 = |Zo|^2 / Z2$$

In some embodiments using a quarter wavelength transmission line to match the power amplifier output impedance to the transmitting antenna (21*a*) input impedance, a transmitting antenna (21*a*) and transmission line (5) may be configured such that the transmitting antenna (21*a*) input impedance Z2 is equal to the square of the transmission line impedance Zo divided by the power amplifier output impedance Z1:

$$Z2 = |Zo|^2 / Z1$$

In some embodiments, impedance matching means for matching the impedance of a transmitting antenna (21a) to the impedance of the power amplifier (13) may comprise a half wavelength transmission line at an operating frequency of the NMR logging apparatus, optionally in conjunction with one or more means to match the transmitting antenna (21a) impedance to the power amplifier impedance. A transmission line (5) whose length is one half wavelength, or any integer multiple of half wavelengths, causes the impedance attached to one end of the transmission line (5) to be reflected without changing on the other end of the transmission line (5), regardless of the characteristic impedance of the transmission line (5). Thus, a half wavelength transmission line can simplify the matching problem to any means that matches the output impedance of the power amplifier (13) to the input impedance of the transmitting antenna (21a). Impedance matching means for use in conjunction with the half wavelength transmission line may include any of the impedance matching means described herein.

Because quarter and/or half wavelength transmission line lengths may be used as impedance matching means as described above, it will be appreciated that in general, impedance matching means may comprises a transmission line length that is approximately a positive integer number of quarter wavelengths of a current and/or voltage waveform generated by the power amplifier, whether the positive integer number is even or odd.

It will be appreciated with the benefit of this disclosure that impedance matching means described herein can be combined in many ways to achieve the purpose of matching the output impedance of the power amplifier (13) to the input impedance of a transmitting antenna (21a) via an electrically long transmission cable. For example, a quarterwave transmission line can be used to achieve a portion of an impedance transformation, and a remaining impedance transformation can be accomplished by an appropriate transformer or other impedance matching circuit. Similarly, the impedance matching means described herein in the context of the power amplifier (13) and the transmitting antenna (21a) may be applied in the context of the power amplifier (13) and a transmitting/receiving antenna (21). Also, the impedance matching means described herein in the context of the power amplifier (13) and the transmitting antenna (21a) may be applied in a receive circuit matching means (28) as well as an impedance matching means deployed at an end of a secondary transmission line (5b) that is opposite the downhole probe (2), e.g., at receive electronics in the surface instrumentation (1).

Figure 9:
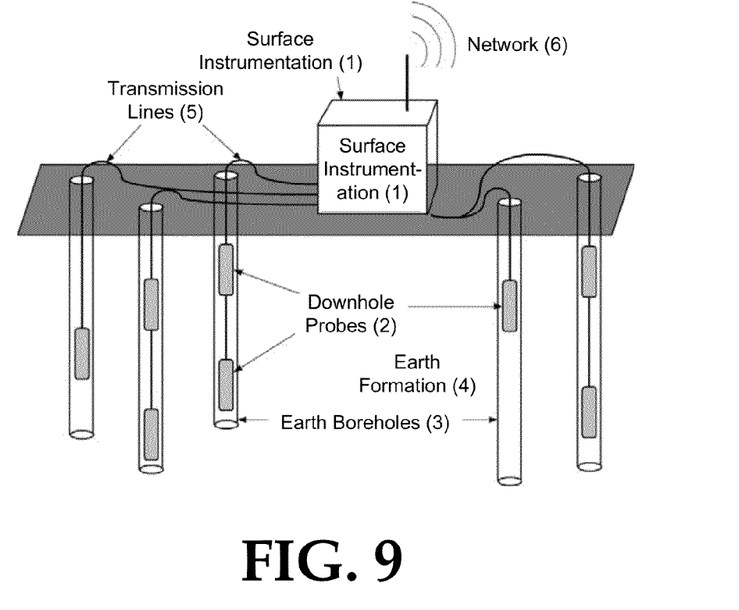
FIG. 9 illustrates an example NMR logging apparatus comprising surface instrumentation, a plurality of transmission lines, and a plurality of downhole probes.

FIG. 9 illustrates an example NMR logging apparatus comprising surface instrumentation (1), a plurality of transmission lines (5), and a plurality of downhole probes (2), in accordance with various embodiments of this disclosure. A plurality of downhole probes (2) and transmission lines (5) are deployed in one or more earth boreholes (3) in an earth formation (4), and surface instrumentation (1) is configured to perform NMR measurements using the plurality of downhole probes (2).

Figure 10:
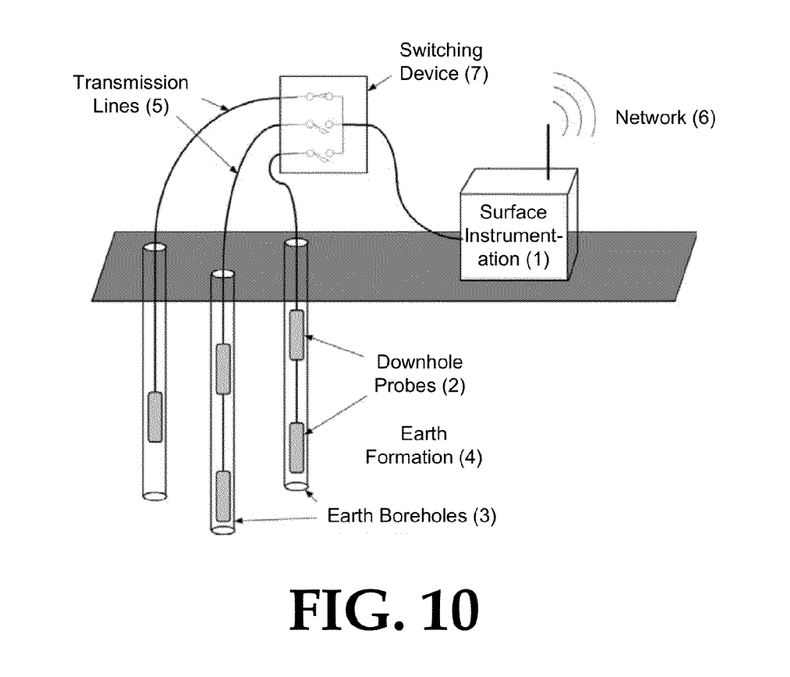
FIG. 10 illustrates an example NMR logging apparatus comprising surface instrumentation, a plurality of transmission lines, a plurality of downhole probes, and a switching device coupled between the transmission lines and the power amplifier to selectively connect the power amplifier to one or more of the transmission lines.

FIG. 10 illustrates an example NMR logging apparatus comprising surface instrumentation (1), a plurality of transmission lines (5), a plurality of downhole probes (2), and a switching device (7) coupled between the transmission lines (5) and the power amplifier (13) to selectively connect the power amplifier (13) to one or more of the transmission lines (5), in accordance with various embodiments of this disclosure.

In FIG. 9 the surface instrumentation (1) may be configured to perform NMR measurements using one or more of the plurality of downhole probes (2). The surface instrumentation (1) may be configured to produce appropriate transmitted NMR pulse sequences, which may be routed to individual downhole probes (2) to perform localized NMR measurements within one or more of the earth boreholes (3). In some embodiments, the surface instrumentation (1) may be configured to perform NMR measurements with the plurality of downhole probes (2) over a common interval of time in which two or more of the downhole probes (2) are used. As shown in FIG. 9, the surface instrumentation (1) may also be configured to perform NMR measurements with two or more of the plurality of downhole probes (2) deployed in a single earth borehole.

Each downhole probe (2) may be connected to the surface instrumentation (1) via a transmission line or lines (5), optionally using one or more of the impedance matching means described herein. Impedance matching means need not be employed on the transmission lines (5). For example, impedance matching means need not be employed when transmission line length is suitably short. The impedance matching means may be common to all downhole probes (2) and transmission lines (5), or unique to each downhole probe (2) and transmission line (5).

In some embodiments, surface instrumentation (1) may comprise a single surface instrumentation unit. In some embodiments, surface instrumentation (1) may control one or more local surface instrumentation units, e.g., by connecting to a communications network (6). Network-enabled surface instrumentation (1) may also enable the surface instrumentation (1) and downhole probes (2) to operate autonomously, and/or from remote locations.

In some embodiments, switching between multiple downhole probes (2) by the surface instrumentation (1) may be accomplished in a number of ways. First, transmission lines for individual downhole probes may be manually attached and detached from the surface instrumentation (1), via appropriate electrical connections. This method facilitates moving the surface instrumentation (1) from one location to another. Hence a single surface instrumentation unit (1) can be used to perform NMR measurements using embedded in-situ downhole probes (2) in multiple locations separated by great distances, potentially as far away as different continents.

Another method for switching between different downhole probes (2) by the surface instrumentation (1) is to use a switching device (7) coupled between the plurality of transmission lines (5) and the power amplifier (13), as depicted in FIG. 10. Switching device (7) may comprise a plurality of electrical switches, whereby switching device (7) may be configured to selectively connect the power amplifier (13) to one or more of the transmission lines (5). The switches may be manually or electrically activated, and may be controlled by a human operator or a computer, such as controller (10). In some embodiments, surface instrumentation (1) may be configured to control the switches of the switching device (7) as appropriate, to perform measurements with one or more of the downhole probes (2). Appropriate impedance matching means may be implemented on either side of each switch in a switching device (7), or on either side of the switching device (7) as a whole, as appropriate for particular embodiments.

In some embodiments, a method for performing NMR measurements within an earth borehole (3) or in earth formations (4) adjacent to an earth borehole, may comprise deploying a plurality of downhole probes (2) with associated transmission lines (5) within a plurality of boreholes (3), and/or at a plurality of locations within a single borehole, and deploying a single surface instrumentation unit or a number of surface instrumentation units less than the number of deployed downhole probes (2) to perform NMR measurements in conjunction with the deployed downhole probes (2). In some embodiments, the surface instrumentation unit or units may be programmed to perform multiple NMR measurements on multiple deployed downhole probes (2) over a common period of time. In some embodiments, the surface instrumentation (1) may be connected to a computer or communications network (6) and monitoring and/or control of NMR measurements may be performed at least in part by human operators at locations remote to the surface instrumentation (1), such as inside a nearby building, or at a location many miles from the location of the surface instrumentation (1).

In some embodiments, one or more downhole probes (2) and transmission lines (5) may be deployed in one or more boreholes (3) and left in said boreholes (3) for significant periods of time, such as weeks, months, or years, so as to enable repeated NMR measurements of the subsurface properties over intervals of time.

In some embodiments, long term NMR monitoring methods may be carried out using NMR logging apparatus described herein. One or more downhole probes (2) and transmission lines (5) may be left in place for extended periods of time, such as weeks, months, or years, and surface instrumentation (1) may be periodically or continuously attached to the one or more transmission lines (5). NMR measurements may be performed by the NMR logging apparatus at various intervals throughout the extended period of time. Long term monitoring has important applications including the monitoring of subsurface contamination, monitoring the remediation of subsurface contamination including bioremediation, monitoring of changes in moisture content in the unsaturated zone, monitoring of formations subject to extraction of oil, gas, water or other commodities, and monitoring of formations subject to injection of carbon dioxide, water or other substances.

In some embodiments, surface instrumentation (1) may be deployed within a mine, cave, underground structure, or other man made or natural cavity within the earth. The surface instrumentation (1) may be deployed and operated within the subsurface cavity and the transmission lines (5) and downhole probes (2) may be deployed into one or more boreholes opening into the subsurface cavity.

There is little distinction left between hardware and software implementations of aspects of systems; the use of hardware or software is generally (but not always) a design choice representing cost vs. efficiency tradeoffs. There are various vehicles by which processes and/or systems and/or other technologies described herein can be effected (e.g., hardware, software, and/or firmware), and that the preferred vehicle may vary with the context in which the processes and/or systems and/or other technologies are deployed. For example, if an implementer determines that speed and accuracy are paramount, the implementer may opt for a mainly hardware and/or firmware vehicle; if flexibility is paramount, the implementer may opt for a mainly software implementation; or, yet again alternatively, the implementer may opt for some combination of hardware, software, and/or firmware.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be within the skill of one skilled in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link, etc.).

Those skilled in the art will recognize that it is common within the art to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity; control motors for moving and/or adjusting components and/or quantities). A typical data processing system may be implemented utilizing any suitable commercially available components, such as those typically found in data computing/communication and/or network computing/communication systems. The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermediate components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

While various embodiments have been disclosed herein, other aspects and embodiments will be apparent to those skilled in art.

The invention claimed is:

1. A Nuclear Magnetic Resonance (NMR) logging apparatus, comprising:
    surface instrumentation comprising a power amplifier configured to generate one or more current and/or voltage waveforms;
    an electrically long transmission line coupled between said power amplifier and a downhole probe, said electrically long transmission line having a length at least one tenth of one wavelength of a current and/or voltage waveform generated by the power amplifier;
    wherein the downhole probe is configured to fit within an earth borehole, the downhole probe comprising:
        one or more static magnetic field generation devices; and
        one or more antennae coupled with the electrically long transmission line; and
    an impedance matching means configured to match an output impedance of the power amplifier through the electrically long transmission line to a load impedance of one or more of the antennae in the downhole probe.

2. The NMR logging apparatus of claim 1, wherein the surface instrumentation further comprises a controller, a signal generator, and receive electronics configured to perform NMR measurements.

3. The NMR logging apparatus of claim 1, wherein the one or more static magnetic field generation devices comprise one or more permanent magnets.

4. The NMR logging apparatus of claim 1, wherein the downhole probe comprises means for coupling energy from the electrically long transmission line into at least one of said antennae.

5. The NMR logging apparatus of claim 1, wherein the downhole probe comprises means for detecting NMR signals induced in at least one of said antennae.

6. The NMR logging apparatus of claim 1, wherein the impedance matching means comprises a first matching means configured to match the output impedance of the power amplifier to a characteristic impedance of the electrically long transmission line, and a second matching means configured to match load impedance of one or more antennae in the downhole probe to the characteristic impedance of the electrically long transmission line.

7. The NMR logging apparatus of claim 6 wherein the first and second matching means are matching circuits comprising transformers, combinations of inductors and capacitors, or combinations of transformers, inductors and capacitors.

8. The NMR logging apparatus of claim 1 wherein the impedance matching means comprises an electrically long transmission line length that is approximately a positive integer number of quarter wavelengths of a current and/or voltage waveform generated by the power amplifier.

9. The NMR logging apparatus of claim 1 wherein the impedance matching means comprises one or more antennae in the downhole probe that are configured to present a load impedance approximately equal to a characteristic impedance of the electrically long transmission line during transmit mode.

10. The NMR logging apparatus of claim 9 wherein the one or more antennae in the downhole probe comprise a pair of inductively coupled loops, such that:
    a first loop is electrically connected to the electrically long transmission line;
    a second loop is electrically connected to a parallel tuning capacitor, a transmit/receive switch, and receive electronics; and
    a ratio of turns between the first and second loops is selected so as to approximately or partially match a relatively high impedance of the second loop to a relatively low impedance of the electrically long transmission line.

11. The NMR logging apparatus of claim 1 further comprising a second electrically long transmission line having a length at least one tenth of one wavelength of the current and/or voltage waveform, wherein the second electrically long transmission line is coupled between the downhole probe and the surface instrumentation to transmit detected NMR signals from the downhole probe to receive electronics among the surface instrumentation.

12. The NMR logging apparatus of claim 11 wherein the downhole probe comprises a preamplifier configured to amplify the detected NMR signals, and wherein an output impedance of the preamplifier is matched to a characteristic impedance of the second electrically long transmission line.

13. The NMR logging apparatus of claim 1 wherein the downhole probe comprises one or more analog to digital converter(s) configured to operate automatically.

14. The NMR logging apparatus of claim 1 wherein the downhole probe comprises one or more analog to digital converter(s) and wherein the surface instrumentation comprises a controller configured to remotely control the one or more analog to digital converter(s).

15. The NMR logging apparatus of claim 1 wherein the surface instrumentation comprises a power supply coupled to the downhole probe via a transmission line.

16. The NMR logging apparatus of claim 1 wherein the downhole probe comprises one or more batteries configured to provide power for electronics within the downhole probe.

17. The NMR logging apparatus of claim 1 wherein the NMR logging apparatus is configured to measure a Nuclear Quadrupole Resonance (NQR) property within and/or surrounding the earth borehole.

18. The NMR logging apparatus of claim 1 wherein the downhole probe includes one or more permanent magnets and a transmit/receive antenna configured to:
generate NMR excitation fields during a transmit mode; and
detect NMR signals in a receive mode.

19. The NMR logging apparatus of claim 1 wherein the downhole probe comprises:
one or more permanent magnets;
a transmitting antenna which is electrically connected to the electrically long transmission line;
a receiving antenna which is electrically connected to receive electronics via a transmit/receive switch; and
wherein the transmitting antenna and receiving antenna are inductively coupled with a non-zero mutual inductance during a transmit mode.

20. The NMR logging apparatus of claim 1 wherein the surface instrumentation is deployed on the surface of the earth, above the surface of the earth, or beneath the surface of the earth in a subsurface cavity or structure wherein the earth borehole opens into said subsurface cavity or structure.

21. The NMR logging apparatus of claim 1 further comprising a plurality of downhole probes coupled with the power amplifier via a plurality of transmission lines, and wherein the surface instrumentation is configured to perform NMR measurements with the plurality of downhole probes.

22. The NMR logging apparatus of claim 21, wherein the surface instrumentation is configured to perform NMR measurements with the plurality of downhole probes over a common interval of time in which two or more of the downhole probes are used.

23. The NMR logging apparatus of claim 22, wherein the surface instrumentation is configured to perform NMR measurements with two or more of the plurality of downhole probes deployed in a single earth borehole.

24. A Nuclear Magnetic Resonance (NMR) logging apparatus, comprising:
surface instrumentation comprising a power amplifier configured to generate one or more current and/or voltage waveforms;
an electrically long transmission line coupled between said power amplifier and a downhole probe, said electrically long transmission line having a length at least one tenth of one wavelength of a current and/or voltage waveform generated by the power amplifier;
wherein the downhole probe is configured to fit within an earth borehole, the downhole probe comprising:
one or more static magnetic field generation devices; and
one or more antennae coupled with the electrically long transmission line; and
one or more impedance matching circuits coupled between the power amplifier and the downhole probe and configured to match an output impedance of the power amplifier through the electrically long transmission line to a load impedance of one or more of the antennae in the downhole probe.

25. A NMR measurement method, comprising:
deploying surface instrumentation on or above an earth surface, said surface instrumentation comprising a power amplifier configured to generate one or more current and/or voltage waveforms;
deploying a downhole probe inside an earth borehole, said downhole probe comprising one or more antennae, and detection means configured to detect NMR signals induced on one or more of said antennae;
deploying a transmission line configured to transfer a current and/or voltage waveform between the power amplifier and the downhole probe, said transmission line having a physical length equal to or greater than one tenth of the wavelength of the transferred current and/or voltage waveform within the transmission line;
deploying an impedance matching means at one or both ends of the transmission line, the impedance matching means configured to match an output impedance of the power amplifier through the transmission line to a load impedance of one or more of the antennae in the downhole probe during a transmit mode; and
using the surface instrumentation and downhole probe coupled via the transmission line and impedance matching means to perform NMR measurements of one or more properties within and/or surrounding the earth borehole.

26. The method of claim 25, wherein the one or more properties comprise one or more of NMR properties, Nuclear Quadrupole Resonance (NQR) properties, physical properties, hydraulic properties, or chemical properties.

27. The method of claim 25, wherein the downhole probe comprises a permanent magnet assembly.

28. A Nuclear Magnetic Resonance (NMR) logging apparatus, comprising:
surface instrumentation, comprising:
a signal generator configured to generate one or more current and/or voltage waveforms; and
an analog to digital (A/D) converter configured to sample one or more detected NMR voltage waveforms;
a transmission line coupled with the surface instrumentation and having a physical length equal to or greater than one tenth of the wavelength of a transferred current and/or voltage waveform within the transmission line;

a downhole probe comprising downhole NMR detection electronics configured to fit within an earth borehole, the downhole NMR detection electronics comprising:
  one or more static magnetic field generation devices; and
  one or more antennae coupled with the transmission line; and
a receive circuit matching means configured to match an output impedance of the downhole NMR detection electronics through the transmission line to either an impedance of the transmission line or an input impedance of the surface instrumentation.

29. The NMR logging apparatus of claim 28, wherein the surface instrumentation comprises a power amplifier configured to generate one or more current and/or voltage waveforms, and further comprising:
  a power amplifier transmission line coupled between the power amplifier and the downhole probe; and
  an impedance matching means configured to match an output impedance of the power amplifier through the power amplifier transmission line to a load impedance of one or more of the antennae in the downhole probe.

30. The NMR logging apparatus of claim 28, further comprising a plurality of downhole probes coupled with the surface instrumentation via a plurality of transmission lines, and wherein the surface instrumentation is configured to perform NMR measurements with the plurality of downhole probes.

31. The NMR logging apparatus of claim 30, wherein the surface instrumentation is configured to perform NMR measurements with the plurality of downhole probes over a common interval of time in which two or more of the downhole probes are used.

32. The NMR logging apparatus of claim 30, wherein the surface instrumentation is configured to perform NMR measurements with two or more of the plurality of downhole probes deployed in a single earth borehole.

33. The method of claim 25, further comprising:
  deploying a plurality of downhole probes inside one or more earth boreholes, each of the downhole probes comprising one or more antennae and detection means configured to detect NMR signals induced on one or more of said antennae;
  deploying a plurality of transmission lines configured to transfer current and/or voltage waveforms between the power amplifier and the downhole probes; and
  using the surface instrumentation and downhole probes coupled via the transmission lines to perform NMR measurements of one or more properties within and/or surrounding the one or more earth boreholes.

34. The method of claim 33, further comprising using at least one of the downhole probes to perform a plurality of NMR measurements at a same location in an earth borehole, wherein said plurality of NMR measurements are separated in time.

35. The method of claim 34, further comprising using the plurality of NMR measurements to detect a change over time of the one or more properties.

36. The method of claim 33, wherein the NMR measurements are performed with the plurality of downhole probes over a common interval of time in which two or more of the downhole probes are used.

37. The method of claim 33, wherein the NMR measurements are performed with two or more of the plurality of downhole probes deployed in a single earth borehole.

38. A NMR measurement method, comprising:
  deploying surface instrumentation on or above the surface of the earth, said surface instrumentation comprising:
    a signal generator configured to generate one or more current and/or voltage waveforms; and
    an analog to digital (A/D) converter configured to sample one or more detected NMR voltage waveforms;
  deploying a downhole probe inside an earth borehole, said downhole probe comprising one or more antennae, and detection means configured to detect NMR signals induced on one or more of said antennae;
  deploying a transmission line configured to transfer a current and/or voltage waveform between the surface instrumentation and the downhole probe, said transmission line having a physical length equal to or greater than one tenth of the wavelength of the transferred current and/or voltage waveform within the transmission line;
  deploying an impedance matching means at one or both ends of the transmission line, the impedance matching means configured to match an output impedance of downhole NMR detection electronics in the downhole probe through the transmission line to either an impedance of the transmission line or an input impedance of the surface instrumentation during a receive mode; and
  using the surface instrumentation and downhole probe coupled via the transmission line and impedance matching means to perform NMR measurements of one or more properties within and/or surrounding the earth borehole.

39. The method of claim 38, wherein the one or more properties comprise one or more of NMR properties, NQR properties, physical properties, hydraulic properties, or chemical properties.

40. The method of claim 38, wherein the downhole probe comprises a permanent magnet assembly.

41. The method of claim 38, wherein the surface instrumentation comprises a power amplifier configured to generate one or more current and/or voltage waveforms, and further comprising deploying a power amplifier transmission line between the power amplifier and the downhole probe.

42. The method of claim 38, further comprising:
  deploying a plurality of downhole probes inside one or more earth boreholes, each of the downhole probes comprising one or more antennae and detection means configured to detect NMR signals induced on one or more of said antennae;
  deploying a plurality of transmission lines configured to transfer current and/or voltage waveforms between the surface instrumentation and the downhole probes; and
  using the surface instrumentation and downhole probes coupled via the transmission lines to perform NMR measurements of one or more properties within and/or surrounding the one or more earth boreholes.

43. The method of claim 42, wherein the NMR measurements are performed with the plurality of downhole probes over a common interval of time in which two or more of the downhole probes are used.

44. The method of claim 42, wherein the NMR measurements are performed with two or more of the plurality of downhole probes deployed in a single earth borehole.

45. The method of claim 42, further comprising using at least one of the downhole probes to perform a plurality of NMR measurements at a same location in an earth borehole, wherein said plurality of NMR measurements are separated in time.

46. The method of claim 45, further comprising using the plurality of NMR measurements to detect a change over time of the one or more properties.

* * * * *